US012558550B2

(12) United States Patent
Zhang et al.

(10) Patent No.: US 12,558,550 B2
(45) Date of Patent: Feb. 24, 2026

(54) SPINAL CORD STIMULATION GUIDING USING EVOKED POTENTIALS

(71) Applicants: Boston Scientific Neuromodulation Corporation, Valencia, CA (US); Research Foundation of the City University of New York, New York, NY (US)

(72) Inventors: Tianhe Zhang, Studio City, CA (US); Rosana Esteller, Santa Clarita, CA (US); Marom Bikson, New York, NY (US)

(73) Assignees: Boston Scientific Neuromodulation Corporation, Valencia, CA (US); Research Foundation of the City University of New York, New York, NY (US)

( * ) Notice: Subject to any disclaimer, the term of this patent is extended or adjusted under 35 U.S.C. 154(b) by 291 days.

(21) Appl. No.: 18/359,682

(22) Filed: Jul. 26, 2023

(65) Prior Publication Data

US 2024/0033525 A1     Feb. 1, 2024

Related U.S. Application Data

(60) Provisional application No. 63/369,882, filed on Jul. 29, 2022.

(51) Int. Cl.
*A61N 1/36* (2006.01)

(52) U.S. Cl.
CPC ..... *A61N 1/36139* (2013.01); *A61N 1/36062* (2017.08); *A61N 1/36071* (2013.01); *A61N 1/36171* (2013.01)

(58) Field of Classification Search
CPC ............ A61N 1/36139; A61N 1/36062; A61N 1/36071; A61N 1/36171
See application file for complete search history.

(56) References Cited

U.S. PATENT DOCUMENTS

| 6,181,969 | B1 | 1/2001 | Gord |
| 6,516,227 | B1 | 2/2003 | Meadows et al. |

(Continued)

FOREIGN PATENT DOCUMENTS

| WO | 2016/176333 A1 | 11/2016 |
| WO | 2020/251899 | 12/2020 |
| WO | 2021/080727 | 4/2021 |

OTHER PUBLICATIONS

International Search Report and Written Opinion regarding corresponding PCT Application No. PCT/US2023/071057, mailed Oct. 17, 2023.

(Continued)

*Primary Examiner* — Paula J Stice
(74) *Attorney, Agent, or Firm* — Lewis & Reese, PLLC

(57) ABSTRACT

Methods and systems for spinal cord stimulation (SCS) are disclosed. The methods and systems involve using electrode leads implanted within the patient's spinal column to record neural responses evoked by the stimulation. The disclosed neural responses are different in several respects from electrical responses that have previously been measured in the context of SCS, such as stimulation artifacts and evoked compound action potentials (ECAPs). The disclosed neural responses typically occur later in time following the evoking stimulation pulse. Another distinguishing feature is that disclosed neural responses are generally most prominently observed with consistent, relatively unchanging amplitudes when the evoking stimulation frequency is ultra-low, for example, about 10 Hz or less. The disclosed methods and systems may use these neural responses as indications of pain, therapy, and/or another clinically relevant dimension, to direct/confirm stimulation placement, and for feedback control of stimulation parameters.

18 Claims, 8 Drawing Sheets

(56) References Cited

U.S. PATENT DOCUMENTS

| | | | |
|---|---|---|---|
| 8,606,362 | B2 | 12/2013 | He et al. |
| 8,620,436 | B2 | 12/2013 | Parramon et al. |
| 9,259,574 | B2 | 2/2016 | Aghassian et al. |
| 10,406,368 | B2 | 9/2019 | Hershey et al. |
| 2012/0092031 | A1 | 4/2012 | Shi et al. |
| 2012/0095519 | A1 | 4/2012 | Parramon et al. |
| 2012/0095529 | A1 | 4/2012 | Parramon et al. |
| 2013/0289665 | A1 | 10/2013 | Marnfeldt et al. |
| 2015/0080982 | A1 | 3/2015 | Funderburk |
| 2015/0157861 | A1 | 6/2015 | Aghassian |
| 2015/0231402 | A1 | 8/2015 | Aghassian |
| 2015/0360038 | A1 | 12/2015 | Zottola et al. |
| 2018/0071520 | A1 | 3/2018 | Weerakoon et al. |
| 2018/0071527 | A1 | 3/2018 | Feldman et al. |
| 2018/0140831 | A1 | 5/2018 | Feldman et al. |
| 2019/0070418 | A1 | 3/2019 | Hincapie Ordonez et al. |
| 2019/0083796 | A1 | 3/2019 | Weerakoon et al. |
| 2019/0099602 | A1 | 4/2019 | Esteller et al. |
| 2019/0175915 | A1 | 6/2019 | Brill et al. |
| 2019/0209844 | A1 | 7/2019 | Esteller et al. |
| 2019/0275331 | A1 | 9/2019 | Zhu |
| 2019/0290900 | A1 | 9/2019 | Esteller et al. |
| 2019/0299006 | A1 | 10/2019 | Marnfeldt |
| 2019/0366094 | A1 | 12/2019 | Esteller et al. |
| 2020/0147393 | A1 | 5/2020 | Zhang et al. |
| 2020/0155019 | A1 | 5/2020 | Esteller et al. |
| 2020/0305744 | A1 | 10/2020 | Weerakoon et al. |
| 2020/0305745 | A1 | 10/2020 | Wagenbach et al. |
| 2020/0324113 | A1 | 10/2020 | Fisher et al. |
| 2020/0376272 | A1 * | 12/2020 | Block ............... A61N 1/36071 |
| 2021/0252287 | A1 | 8/2021 | Esteller et al. |
| 2021/0252289 | A1 | 8/2021 | Esteller |
| 2022/0233866 | A1 | 7/2022 | Gururaj et al. |
| 2022/0323764 | A1 | 10/2022 | Esteller et al. |
| 2022/0347479 | A1 | 11/2022 | Esteller et al. |

OTHER PUBLICATIONS

Gmel, Gerrit Eduard, et al., "The Effect of Spinal Cord Stimulation Frequency on the Neural Response and Perceived Sensation in Patients with Chronic Pain," Frontiers in Neuroscience, vol. 15, Article 625835, Jan. 2021, 8 pages.
"Preparation of Calibration Curves, A Guide to Best Practice," LGC Limited 2003, LGC/VAM/2003/032, Department of Trade and Industry as part of the National Measurement System Valid Analytical Measurement (VAM) Program,. Sep. 2003, 30 pages.

* cited by examiner

SPINAL CORD STIMULATION GUIDING USING EVOKED POTENTIALS

CROSS REFERENCE TO RELATED APPLICATIONS

This is a non-provisional of U.S. Provisional Patent Application Ser. No. 63/369,882, filed Jul. 29, 2022, to which priority is claimed, and which is incorporated herein by reference.

FIELD OF THE INVENTION

This application relates to Implantable Medical Devices (IMDs), and more specifically sensing signals in an implantable stimulator device.

INTRODUCTION

Implantable neurostimulator devices are implantable medical devices (IMDs) that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable neurostimulator device system.

An SCS system typically includes an Implantable Pulse Generator (IPG) 10 shown in FIG. 1. The IPG 10 includes a biocompatible device case 12 that holds the circuitry and a battery 14 for providing power for the IPG to function. The IPG 10 is coupled to tissue-stimulating electrodes 16 via one or more electrode leads that form an electrode array 17. For example, one or more percutaneous leads 15 can be used having ring-shaped or split-ring electrodes 16 carried on a flexible body 18. In another example, a paddle lead 19 provides electrodes 16 positioned on one of its generally flat surfaces. Lead wires 20 within the leads are coupled to the electrodes 16 and to proximal contacts 21 insertable into lead connectors 22 fixed in a header 23 on the IPG 10, which header can comprise an epoxy for example. Once inserted, the proximal contacts 21 connect to header contacts 24 within the lead connectors 22, which are in turn coupled by feedthrough pins through a case feedthrough 26 to stimulation circuitry 28 within the case 12.

In the illustrated IPG 10, there are thirty-two electrodes (E1-E32), split between four percutaneous leads 15, or contained on a single paddle lead 19, and thus the header 23 may include a 2×2 array of eight-electrode lead connectors 22. However, the type and number of leads, and the number of electrodes, in an IPG is application-specific and therefore can vary. The conductive case 12 can also comprise an electrode (Ec). In a SCS application, the electrode lead(s) are typically implanted in the spinal column proximate to the dura in a patient's spinal cord, preferably spanning left and right of the patient's spinal column. The proximal contacts 21 are tunneled through the patient's tissue to a distant location such as the buttocks where the IPG case 12 is implanted, at which point they are coupled to the lead connectors 22. In other IPG examples designed for implantation directly at a site requiring stimulation, the IPG can be lead-less, having electrodes 16 instead appearing on the body of the IPG 10 for contacting the patient's tissue. The IPG lead(s) can be integrated with and permanently connected to the IPG 10 in other solutions. The goal of SCS therapy is to provide electrical stimulation from the electrodes 16 to alleviate a patient's symptoms, such as chronic back pain.

IPG 10 can include an antenna 27a allowing it to communicate bi-directionally with a number of external devices used to program or monitor the IPG, such as a hand-held patient controller or a clinician's programmer, as described for example in U.S. Patent Application Publication 2019/0175915. Antenna 27a as shown comprises a conductive coil within the case 12, although the coil antenna 27a can also appear in the header 23. When antenna 27a is configured as a coil, communication with external devices preferably occurs using near-field magnetic induction. IPG 10 may also include a Radio-Frequency (RF) antenna 27b. In FIG. 1, RF antenna 27b is shown within the header 23, but it may also be within the case 12. RF antenna 27b may comprise a patch, slot, or wire, and may operate as a monopole or dipole. RF antenna 27b preferably communicates using far-field electromagnetic waves, and may operate in accordance with any number of known RF communication standards, such as Bluetooth, Zigbee, MICS, and the like.

Stimulation in IPG 10 is typically provided by pulses each of which may include a number of phases such as 30a and 30b, as shown in the example of FIG. 2A. Stimulation parameters typically include amplitude (current I, although a voltage amplitude V can also be used); frequency (F); pulse width (PW) of the pulses or of its individual phases; the electrodes 16 selected to provide the stimulation; and the polarity of such selected electrodes, i.e., whether they act as anodes that source current to the tissue or cathodes that sink current from the tissue. These and possibly other stimulation parameters taken together comprise a stimulation program that the stimulation circuitry 28 in the IPG 10 can execute to provide therapeutic stimulation to a patient.

In the example of FIG. 2A, electrode E4 has been selected as an anode (during its first phase 30a), and thus provides pulses which source a positive current of amplitude +I to the tissue. Electrode E5 has been selected as a cathode (again during first phase 30a), and thus provides pulses which sink a corresponding negative current of amplitude –I from the tissue. This is an example of bipolar stimulation, in which only two lead-based electrodes are used to provide stimulation to the tissue (one anode, one cathode). However, more than one electrode may be selected to act as an anode at a given time, and more than one electrode may be selected to act as a cathode at a given time. The case electrode Ec (12) can also be selected as an electrode, or current return, in what is known as monopolar situation.

IPG 10 as mentioned includes stimulation circuitry 28 to form prescribed stimulation at a patient's tissue. FIG. 3 shows an example of stimulation circuitry 28, which includes one or more current source circuits $40_i$ and one or more current sink circuits $42_i$. The sources and sinks $40_i$ and $42_i$ can comprise Digital-to-Analog converters (DACs), and may be referred to as PDACs $40_i$ and NDACs $42_i$ in accordance with the Positive (sourced, anodic) and Negative (sunk, cathodic) currents they respectively issue. In the example shown, a NDAC/PDAC $40_i/42_i$ pair is dedicated (hardwired) to a particular electrode node ei 39. Each electrode node ei 39 is connected to an electrode Ei 16 via a DC-blocking capacitor Ci 38, for the reasons explained below. The stimulation circuitry 28 in this example also supports selection of the conductive case 12 as an electrode (Ec 12), which case electrode is typically selected for monopolar stimulation. PDACs and NDACs 42$_i$ can also comprise voltage sources.

Proper control of the PDACs 40$_i$ and NDACs 42$_i$ allows any of the electrodes 16 to act as anodes or cathodes to create a current through a patient's tissue, R, hopefully with good therapeutic effect. In the example shown (FIG. 2A), and during the first phase 30$a$ in which electrodes E4 and E5 are selected as an anode and cathode respectively, PDAC 40$_4$ and NDAC 42$_5$ are activated and digitally programmed to produce the desired current, I, with the correct timing (e.g., in accordance with the prescribed frequency F and pulse width PWa). During the second phase 30$b$ (PWb), PDAC 40$_5$ and NDAC 42$_4$ would be activated to reverse the polarity of the current. More than one anode electrode and more than one cathode electrode may be selected at one time, and thus current can flow through the tissue R between two or more of the electrodes 16.

Power for the stimulation circuitry 28 is provided by a compliance voltage VH. As described in further detail in U.S. Patent Application Publication 2013/0289665, the compliance voltage VH can be produced by a compliance voltage generator 29, which can comprise a circuit used to boost the battery 14's voltage (Vbat) to a voltage VH sufficient to drive the prescribed current I through the tissue R. The compliance voltage generator 29 may comprise an inductor-based boost converter as described in the '665 Publication, or can comprise a capacitor-based charge pump. Because the resistance of the tissue is variable, VH may also be variable, and can be as high as 18 Volts in one example.

Other stimulation circuitries 28 can also be used in the IPG 10. In an example not shown, a switching matrix can intervene between the one or more PDACs 40$_i$ and the electrode nodes ei 39, and between the one or more NDACs 42$_i$ and the electrode nodes. Switching matrices allow one or more of the PDACs or one or more of the NDACs to be connected to one or more anode or cathode electrode nodes at a given time. Various examples of stimulation circuitries can be found in U.S. Pat. Nos. 6,181,969, 8,606,362, 8,620,436, and U.S. Patent Application Publications 2018/0071520 and 2019/0083796. Much of the stimulation circuitry 28 of FIG. 3, including the PDACs 40$_i$ and NDACs 42$_i$ the switch matrices (if present), and the electrode nodes ei 39 can be integrated on one or more Application Specific Integrated Circuits (ASICs), as described in U.S. Patent Application Publications 2012/0095529, 2012/0092031, and 2012/0095519, which are incorporated by reference. As explained in these references, ASIC(s) may also contain other circuitry useful in the IPG 10, such as telemetry circuitry (for interfacing off chip with telemetry antennas 27$a$ and/or 27$b$), the compliance voltage generator 29, various measurement circuits, etc.

Also shown in FIG. 3 are DC-blocking capacitors Ci 38 placed in series in the electrode current paths between each of the electrode nodes ei 39 and the electrodes Ei 16 (including the case electrode Ec 12). The DC-blocking capacitors 38 act as a safety measure to prevent DC current injection into the patient, as could occur for example if there is a circuit fault in the stimulation circuitry 28. The DC-blocking capacitors 38 are typically provided off-chip (off of the ASIC(s)), and instead may be provided in or on a circuit board in the IPG 10 used to integrate its various components, as explained in U.S. Patent Application Publication 2015/0157861.

Although not shown, circuitry in the IPG 10 including the stimulation circuitry 28 can also be included in an External Trial Stimulator (ETS) device which is used to mimic operation of the IPG during a trial period and prior to the IPG 10's implantation. An ETS device is typically used after the electrode array 17 has been implanted in the patient. The proximal ends of the leads in the electrode array 17 pass through an incision in the patient and are connected to the externally-worn ETS, thus allowing the ETS to provide stimulation to the patient during the trial period. Further details concerning an ETS device are described in U.S. Pat. No. 9,259,574 and U.S. Patent Application Publication 2019/0175915.

Referring again to FIG. 2A, the stimulation pulses as shown are biphasic, with each pulse at each electrode comprising a first phase 30$a$ followed thereafter by a second phase 30$b$ of opposite polarity. Biphasic pulses are useful to actively recover any charge that might be stored on capacitive elements in the electrode current paths, such as the DC-blocking capacitors 38, the electrode/tissue interface, or within the tissue itself. To recover all charge by the end of the second pulse phase 30$b$ of each pulse (Vc4=Vc5=0V), the first and second phases 30$a$ and 30$b$ are preferably charged balanced at each electrode, with the phases comprising an equal amount of charge but of the opposite polarity. In the example shown, such charge balancing is achieved by using the same pulse width (PWa=PWb) and the same amplitude=(|+I|=|−I|) for each of the pulse phases 30$a$ and 30$b$. However, the pulse phases 30$a$ and 30$b$ may also be charged balance if the product of the amplitude and pulse widths of the two phases 30$a$ and 30$b$ are equal, as is known.

FIG. 3 shows that stimulation circuitry 28 can include passive recovery switches 41$_i$ which are described further in U.S. Patent Application Publications 2018/0071527 and 2018/0140831. Passive recovery switches 41$_i$ may be attached to each of the electrode nodes 39, and are used to passively recover any charge remaining on the DC-blocking capacitors Ci 38 after issuance of the second pulse phase 30$b$—i.e., to recover charge without actively driving a current using the DAC circuitry. Passive charge recovery can be prudent, because non-idealities in the stimulation circuitry 28 may lead to pulse phases 30$a$ and 30$b$ that are not perfectly charge balanced. Passive charge recovery typically occurs during at least a portion 30$c$ (FIG. 2A) of the quiet periods between the pulses by closing passive recovery switches 41$_i$. As shown in FIG. 3, the other end of the switches 41$_i$ not coupled to the electrode nodes 39 are connected to a common reference voltage, which in this example comprises the voltage of the battery 14, Vbat, although another reference voltage could be used. As explained in the above-cited references, passive charge recovery tends to equilibrate the charge on the DC-blocking capacitors 38 and other capacitive elements by placing the capacitors in parallel between the reference voltage (Vbat) and the patient's tissue. Note that passive charge recovery is illustrated as small exponentially-decaying curves during 30c in FIG. 2A, which may be positive or negative depending on whether pulse phase 30$a$ or 30$b$ has a predominance of charge at a given electrode.

FIG. 4 shows various external devices that can wirelessly communicate data with the IPG 10 and/or the ETS 80, including a patient, hand-held external controller 45, and a clinician programmer 50. Both of devices 45 and 50 can be used to wirelessly send a stimulation program to the IPG 10 or ETS 80—that is, to program their stimulation circuitries 28 and 44 to produce pulses with a desired shape and timing described earlier. Both devices 45 and 50 may also be used to adjust one or more stimulation parameters of a stimulation program that the IPG 10 or ETS 80 is currently executing. Devices 45 and 50 may also receive information from the IPG 10 or ETS such as various status information, etc.

External controller 45 can be as described in U.S. Patent Application Publication 2015/0080982 for example, and may comprise either a dedicated controller configured to work with the IPG 10. External controller 45 may also comprise a general purpose mobile electronics device such as a mobile phone which has been programmed with a Medical Device Application (MDA) allowing it to work as a wireless controller for the IPG 10 or ETS 80, as described in U.S. Patent Application Publication 2015/0231402. External controller 45 includes a user interface, including means for entering commands (e.g., buttons or icons) and a display 46. The external controller 45's user interface enables a patient to adjust stimulation parameters, although it may have limited functionality when compared to the more-powerful clinician programmer 50, described shortly.

The external controller 45 can have one or more antennas capable of communicating with the IPG 10 and ETS 80. For example, the external controller 45 can have a near-field magnetic-induction coil antenna 47a capable of wirelessly communicating with the coil antenna 27a or 42a in the IPG 10 or ETS 80. The external controller 45 can also have a far-field RF antenna 47b capable of wirelessly communicating with the RF antenna 27b or 42b in the IPG 10 or ETS 80.

The external controller 45 can also have control circuitry 48 such as a microprocessor, microcomputer, an FPGA, other digital logic structures, etc., which is capable of executing instructions in an electronic device. Control circuitry 48 can for example receive patient adjustments to stimulation parameters, and create a stimulation program to be wirelessly transmitted to the IPG 10 or ETS 80.

Clinician programmer 50 is described further in U.S. Patent Application Publication 2015/0360038, and is only briefly explained here. The clinician programmer 50 can comprise a computing device 51, such as a desktop, laptop, or notebook computer, a tablet, a mobile smart phone, a Personal Data Assistant (PDA)-type mobile computing device, etc. In FIG. 4, computing device 51 is shown as a laptop computer that includes typical computer user interface means such as a screen 52, a mouse, a keyboard, speakers, a stylus, a printer, etc., not all of which are shown for convenience. Also shown in FIG. 4 are accessory devices for the clinician programmer 50 that are usually specific to its operation as a stimulation controller, such as a communication "wand" 54, and a joystick 58, which are coupleable to suitable ports on the computing device 51, such as USB ports 59 for example.

The antenna used in the clinician programmer 50 to communicate with the IPG 10 or ETS can depend on the type of antennas included in those devices. If the patient's IPG 10 or ETS includes a coil antenna 27a or 82a, wand 54 can likewise include a coil antenna 56a to establish near-filed magnetic-induction communications at small distances. In this instance, the wand 54 may be affixed in close proximity to the patient, such as by placing the wand 54 in a belt or holster wearable by the patient and proximate to the patient's IPG 10 or ETS 80. If the IPG 10 or ETS 80 includes an RF antenna 27b or 82b, the wand 54, the computing device 51, or both, can likewise include an RF antenna 56b to establish communication with the IPG 10 or ETS 80 at larger distances. (Wand 54 may not be necessary in this circumstance). The clinician programmer 50 can also establish communication with other devices and networks, such as the Internet, either wirelessly or via a wired link provided at an Ethernet or network port.

To program stimulation programs or parameters for the IPG 10 or ETS 80, the clinician interfaces with a clinician programmer graphical user interface (GUI) 64 provided on the display 52 of the computing device 51. As one skilled in the art understands, the GUI 64 can be rendered by execution of clinician programmer software 66 on the computing device 51, which software may be stored in the device's non-volatile memory 68. One skilled in the art will additionally recognize that execution of the clinician programmer software 66 in the computing device 51 can be facilitated by controller circuitry 70 such as a microprocessor, microcomputer, an FPGA, other digital logic structures, etc., which is capable of executing programs in a computing device. In one example, controller circuitry 70 can include any of the i5 Core Processors, manufactured by Intel Corp. Such controller circuitry 70, in addition to executing the clinician programmer software 66 and rendering the GUI 64, can also enable communications via antennas 56a or 56b to communicate stimulation parameters chosen through the GUI 64 to the patient's IPG 10.

While GUI 64 is shown as operating in the clinician programmer 50, the user interface of the external controller 45 may provide similar functionality as the external controller 45 may have similar controller circuitry, software, etc.

SUMMARY

Disclosed herein is a system for providing electrical stimulation to a patient's spinal cord to treat pain in the patient using one or more electrode leads implantable in the patient's spinal column, each electrode lead comprising a plurality of spinal electrode contacts, the system comprising: a neurostimulator that is connectable to the one or more electrode leads, and control circuitry configured to: use a first one or more of the spinal electrode contacts to provide evoking stimulation to the patient's spinal cord, wherein the evoking stimulation has a frequency of 50 Hz or less, and use a second one or more of the spinal electrode contacts to sense and record the ESP. According to some embodiments, the evoking stimulation has a frequency of 10 Hz or less. According to some embodiments, the evoking stimulation is also configured to provide pain relief for the patient. According to some embodiments, the evoking stimulation is configured to be sub-perception. According to some embodiments, the control circuitry is configured to use a third one or more of the electrodes to provide therapeutic stimulation to the patient's spinal cord, wherein the therapeutic stimulation has a frequency of greater than 30 Hz. According to some embodiments, the third one or more of the electrodes is different than the first one or more electrodes. According to some embodiments, the third one or more of the electrodes is the same as the first one or more of the electrodes and wherein providing the therapeutic stimulation and the evoking stimulation comprises: using the first one or more electrodes to provide the therapeutic stimulation for a first duration, following the first duration, applying no stimulation for a second duration at the first one or more electrodes, and following the second duration, using the first one or more electrodes to provide the evoking stimulation. According to some embodiments, the therapeutic stimulation is configured to provide pain relief to the patient. According to some embodiments, the therapeutic stimulation is configured to provide paresthesia-pain overlap. According to some embodiments, the therapeutic stimulation is sub-perception. According to some embodiments, the therapeutic stimulation is paresthesia-based. According to some embodiments, the control circuitry is configured to determine one or more features of the ESP. According to some embodiments, the control circuitry is configured to use the one or more features for closed loop feedback adjustment of therapeutic stimulation. According to some embodiments, the closed loop feedback adjustment is configured to maintain the therapeutic stimulation within a therapeutic window. According to some embodiments, the closed loop feedback adjustment is configured to maintain paresthesia-pain overlap.

Also disclosed herein is a method of sensing an evoked synaptic potential (ESP) evoked in a patient's spinal cord in response to stimulation applied to the patient's spinal cord using one or more electrode leads implantable in the patient's spinal column, each electrode lead comprising a plurality of spinal electrode contacts, the method comprising: using a first one or more of the spinal electrode contacts to provide evoking stimulation to the patient's spinal cord, wherein the evoking stimulation has a frequency of 50 Hz or less, and using a second one or more of the spinal electrode contacts to sense and record the ESP. According to some embodiments, the evoking stimulation has a frequency of 10 Hz or less. According to some embodiments, the evoking stimulation is also configured to provide pain relief for the patient. According to some embodiments, the evoking stimulation is configured to be sub-perception. According to some embodiments, the method further comprises using a third one or more of the electrodes to provide therapeutic stimulation to the patient's spinal cord, wherein the therapeutic stimulation has a frequency of greater than 30 Hz. According to some embodiments, the third one or more of the electrodes is different than the first one or more electrodes. According to some embodiments, the third one or more of the electrodes is the same as the first one or more of the electrodes and wherein providing the therapeutic stimulation and the evoking stimulation comprises: using the first one or more electrodes to provide the therapeutic stimulation for a first duration, following the first duration, applying no stimulation for a second duration at the first one or more electrodes, and following the second duration, using the first one or more electrodes to provide the evoking stimulation. According to some embodiments, the therapeutic stimulation is configured to provide pain relief to the patient. According to some embodiments, the therapeutic stimulation is configured to provide paresthesia-pain overlap. According to some embodiments, the therapeutic stimulation is sub-perception. According to some embodiments, the therapeutic stimulation is paresthesia-based. According to some embodiments, the method further comprises determining one or more features of the ESP. According to some embodiments, the method further comprises using the one or more features for closed loop feedback adjustment of therapeutic stimulation. According to some embodiments, the closed loop feedback adjustment is configured to maintain the therapeutic stimulation within a therapeutic window. According to some embodiments, the closed loop feedback adjustment is configured to maintain paresthesia-pain overlap.

Also disclosed herein is a system for providing electrical stimulation to a patient's spinal cord to treat pain in the patient using one or more electrode leads implantable in the patient's spinal column, each electrode lead comprising a plurality of spinal electrode contacts, the system comprising: a neurostimulator that is connectable to the one or more electrode leads, and control circuitry configured to: use a first one or more of the spinal electrode contacts to issue evoking stimulation to the patient's spinal cord, and following a delay of at least 2 milliseconds from the issuance of the evoking stimulation, use a second one or more of the spinal electrode contacts to sense the ESP. According to some embodiments, the delay is at least 2.5 milliseconds from the issuance of the evoking stimulation. According to some embodiments, the control circuitry is configured to: following the issuance of the evoking stimulation, and prior to sensing the ESP, use a third one or more of the spinal electrode contacts to sense an evoked compound action potential (ECAP) evoked in a patient's spinal cord in response to stimulation, wherein the third one or more electrodes are the same or different than the second one or more electrodes. According to some embodiments, the delay is determined with respect to a feature of the sensed ECAP. According to some embodiments, the control circuitry is configured to: following the issuance of the evoking stimulation, and prior to sensing the ESP, use a third one or more of the spinal electrode contacts to sense a stimulation artifact, wherein the third one or more electrodes are the same or different than the second one or more electrodes. According to some embodiments, the delay is determined with respect to a feature of the stimulation artifact. According to some embodiments, using a second one or more of the spinal electrode contacts to sense the ESP comprises sensing for at least 5 milliseconds. According to some embodiments, using a second one or more of the spinal electrode contacts to sense the ESP comprises sensing for at least 10 milliseconds. According to some embodiments, the evoking stimulation has a frequency of 10 Hz or less. According to some embodiments, the evoking stimulation has a frequency of 5 Hz or less. According to some embodiments, the control circuitry is configured to use a third one or more of the spinal electrode contacts to issue therapeutic stimulation to the patient's spinal cord. According to some embodiments, the therapeutic stimulation has a frequency of greater than 50 Hz. According to some embodiments, the third one or more of the electrodes is different than the first one or more electrodes. According to some embodiments, the third one or more of the electrodes is the same as the first one or more of the electrodes. According to some embodiments, the therapeutic stimulation is configured to provide pain relief to the patient. According to some embodiments, the therapeutic stimulation is configured to provide paresthesia-pain overlap. According to some embodiments, the therapeutic stimulation is sub-perception. According to some embodiments, the therapeutic stimulation is paresthesia-based. According to some embodiments, the control circuitry is configured to determine one or more features of the ESP. According to some embodiments, the control circuitry is configured to use the one or more features for closed loop feedback adjustment of therapeutic stimulation. According to some embodiments, the closed loop feedback adjustment is configured to maintain the therapeutic stimulation within a therapeutic window. According to some embodiments, the closed loop feedback adjustment is configured to maintain paresthesia-pain overlap.

Also disclosed herein is a method of sensing an evoked synaptic potential (ESP) evoked in a patient's spinal cord in response to stimulation applied to the patient's spinal cord using one or more electrode leads implantable in the patient's spinal column, each electrode lead comprising a plurality of spinal electrode contacts, the method comprising: using a first one or more of the spinal electrode contacts to issue evoking stimulation to the patient's spinal cord, following a delay of at least 2 milliseconds from the issuance of the evoking stimulation, using a second one or more of the spinal electrode contacts to sense the ESP. According to some embodiments, the delay is at least 2.5 milliseconds from the issuance of the evoking stimulation. According to some embodiments, the method further comprises: following the issuance of the evoking stimulation, and prior to sensing the ESP, using a third one or more of the spinal electrode contacts to sense an evoked compound action potential (ECAP) evoked in a patient's spinal cord in response to stimulation. According to some embodiments, the delay is determined with respect to a feature of the sensed ECAP. According to some embodiments, the method further comprises: following the issuance of the evoking stimulation, and prior to sensing the ESP, using a third one or more of the spinal electrode contacts to sense a stimulation artifact. According to some embodiments, the delay is determined with respect to a feature of the stimulation artifact. According to some embodiments, using a second one or more of the spinal electrode contacts to sense the ESP comprises sensing for at least 5 milliseconds. According to some embodiments, using a second one or more of the spinal electrode contacts to sense the ESP comprises sensing for at least 10 milliseconds. According to some embodiments, the evoking stimulation has a frequency of 10 Hz or less. According to some embodiments, the evoking stimulation has a frequency of 5 Hz or less. According to some embodiments, using a third one or more of the spinal electrode contacts to issue therapeutic stimulation to the patient's spinal cord. According to some embodiments, the therapeutic stimulation has a frequency of greater than 50 Hz. According to some embodiments, the third one or more of the electrodes is different than the first one or more electrodes. According to some embodiments, the third one or more of the electrodes is the same as the first one or more of the electrodes. According to some embodiments, the therapeutic stimulation is configured to provide pain relief to the patient. According to some embodiments, the therapeutic stimulation is configured to provide paresthesia-pain overlap. According to some embodiments, the therapeutic stimulation is sub-perception. According to some embodiments, the therapeutic stimulation is supra-perception. According to some embodiments, the method further comprises determining one or more features of the ESP. According to some embodiments, the method further comprises using the one or more features for closed loop feedback adjustment of therapeutic stimulation. According to some embodiments, the closed loop feedback adjustment is configured to maintain the therapeutic stimulation within a therapeutic window. According to some embodiments, the closed loop feedback adjustment is configured to maintain paresthesia-pain overlap.

The invention may also reside in the form of a programed external device (via its control circuitry) for carrying out the above methods, a programmed IPG or ETS (via its control circuitry) for carrying out the above methods, a system including a programmed external device and IPG or ETS for carrying out the above methods, or as a computer readable media for carrying out the above methods stored in an external device or IPG or ETS.

DETAILED DESCRIPTION

Figure 5:
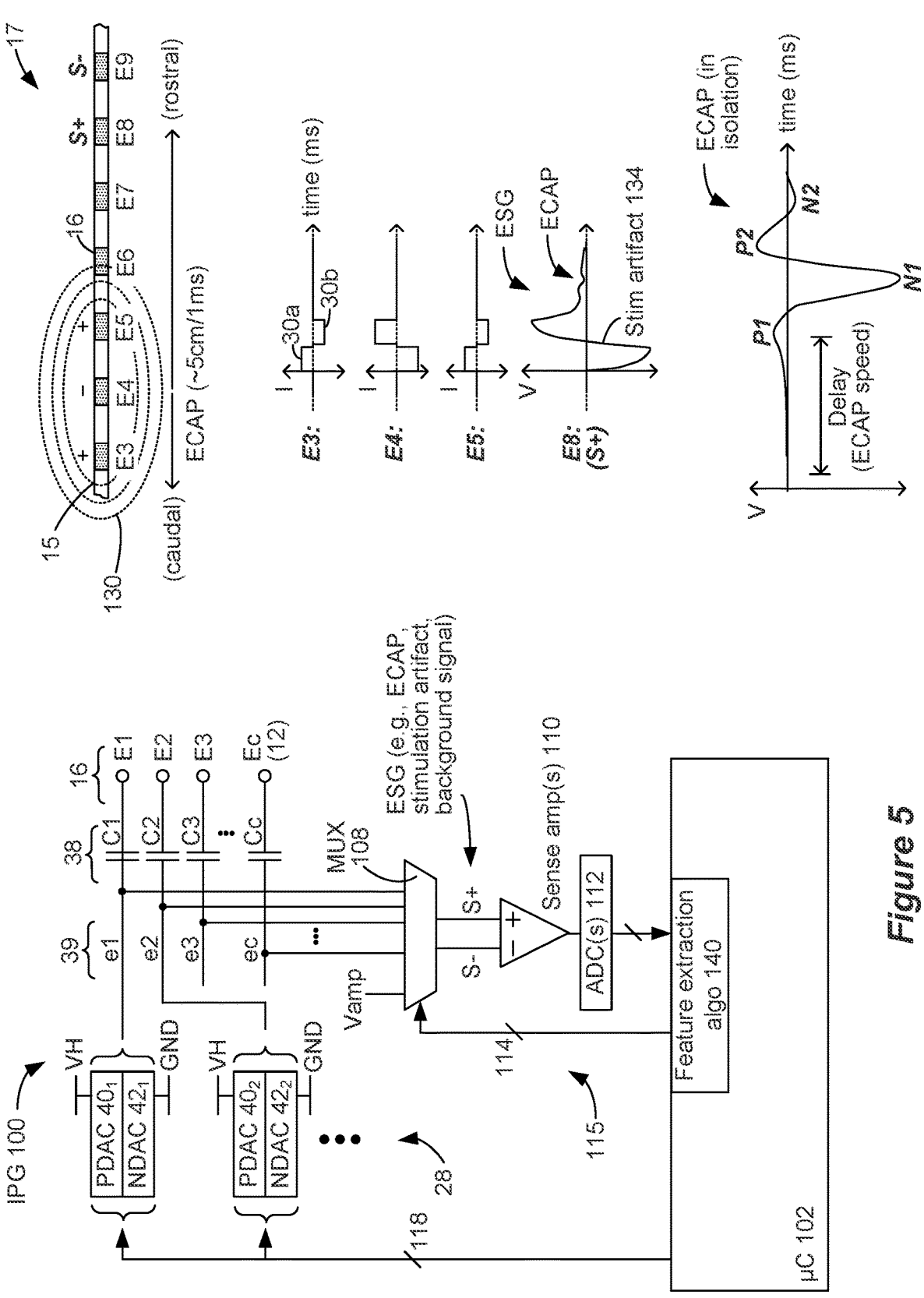
FIG. 5 shows an improved IPG having stimulation capability and the ability to sense an ElectroSpinoGram (ESG) signal which may include Evoked Compound Action Potentials (ECAPs) caused by the simulation.

An increasingly interesting development in pulse generator systems, and in Spinal Cord Stimulator (SCS) pulse generator systems specifically, is the addition of sensing capability to complement the stimulation that such systems provide. FIG. 5 shows an IPG 100 that includes stimulation and sensing functionality. An ETS as described earlier may also include stimulation and sensing capabilities, and the circuitry shown in FIG. 5.

For example, it can be beneficial to sense a neural response in neural tissue that has received stimulation from the IPG 100. One such neural response is an Evoked Compound Action Potential (ECAP). An ECAP comprises a cumulative response provided by neural fibers that are recruited by the stimulation, and essentially comprises the sum of the action potentials of recruited neural elements (ganglia or fibers) when they "fire." An ECAP is shown in isolation in FIG. 5, and comprises a number of peaks that are conventionally labeled with P for positive peaks and N for negative peaks, with P1 comprising a first positive peak, N1 a first negative peak, P2 a second positive peak, N2 a second negative peak, and so on. Note that not all ECAPs will have the exact shape and number of peaks as illustrated in FIG. 5, because an ECAP's shape is a function of the number and types of neural elements that are recruited and that are involved in its conduction. An ECAP is generally a small signal, and may have a peak-to-peak amplitude on the order of hundreds of microvolts or more.

FIG. 5 also shows an electrode array 17 comprising (in this example) a single percutaneous lead 15, and shows use of electrodes E3, E4 and E5 to produce pulses in a tripolar mode of stimulation, with (during the first phase 30a) E3 and E5 comprising anodes and E4 a cathode. Other electrode arrangements (e.g., bipoles, etc.) could be used as well. Such stimulation produces an electric field 130 in a volume of the patient's tissue centered around the selected electrodes. Some of the neural fibers within the electric field 130 will be recruited and fire, particularly those proximate to the cathodic electrode E4, forming ECAPs which can travel both rostrally toward the brain and caudally away from the brain. The ECAPs pass through the spinal cord by neural conduction with a speed which is dependent on the neural fibers involved in the conduction. In one example, the ECAP may move at a speed of about 5 cm/1 ms. U.S. Patent Application Publication 2020/0155019, describes a lead that can be useful in the detection of ECAPs.

ECAPs can be sensed at one or more sensing electrodes which can be selected from the electrodes 16 in the electrode array 17. Sensing preferably occurs differentially, with one electrode (e.g., S+, E8) used for sensing and another (e.g., S−, E9) used as a reference. This could also be flipped, with E8 providing the reference (S−) for sensing at electrode E9 (S+). Although not shown, the case electrode Ec (12) can also be used as a sensing reference electrode S−. Sensing reference S− could also comprise a fixed voltage provided by the IPG 100 (e.g., Vamp, discussed below), such as ground, in which case sensing would be said to be single-ended instead of differential.

The waveform appearing at sensing electrode E8 (S+) is shown in FIG. 5, which includes a stimulation artifact 134 as well as an ECAP. The stimulation artifact 134 comprises a voltage that is formed in the tissue as a result of the stimulation, i.e., as a result of the electric field 130 that the stimulation creates in the tissue. As described in U.S. Patent Application Publication 2019/0299006, the voltage in the tissue can vary between ground and the compliance voltage VH used to power the DACs, and so the stimulation artifact 134 can be on the order of Volts, and therefore significantly higher than the magnitude of stimulation-induced ECAPs. Generally speaking, the waveform sensed at the sensing electrode may be referred to as an ElectroSpinoGram (ESG) signal, which comprises the ECAP, the stimulation artifact 134, and other background signals that may be produced by neural tissue even absent stimulation. Realize that the ESG signal as shown at the sensing electrode S+ in FIG. 5 is idealized. The figures in U.S. Patent Application Publication 2022/0323764 show actual recorded ESG traces.

The magnitudes of the stimulation artifact 134 and the ECAP at the sensing electrodes S+ and S− are dependent on many factors, such as the strength of the stimulation, and the distance of sensing electrodes from the stimulation. ECAPs tend to decrease in magnitude at increasing stimulation-to-sensing distances because they disperse in the tissue. Stimulation artifacts 134 also decrease in magnitude at increasing stimulation-to-sensing distances because the electric field 130 is weaker at further distances. Note that the stimulation artifact 134 is also generally larger during the provision of the pulses, although it may still be present even after the pulse (i.e., the last phase of the pulse) has ceased, due to the capacitive nature of the tissue or the capacitive nature of the driving circuitry (i.e., the DACs). As a result, the electric field 130 may not dissipate immediately upon cessation of the pulse.

It can be useful to sense in the IPG 100 features of either or both of the ECAPs or stimulation artifact 134 contained within the sensed ESG signal, because such features can be used to useful ends. For example, ECAP features can be used for feedback, such as closed-loop feedback, to adjust the stimulation the IPG 100 provides. See, e.g., U.S. Pat. No. 10,406,368; U.S. Patent Application Publications 2019/0099602, 2019/0209844, 2021/0252287, 2021/0252289, 2019/0070418, 2020/0147393 and 2022/0347479. ECAP assessment can also be used to infer the types of neural elements or fibers that are recruited, which can in turn be used to adjust the stimulation to selectively stimulate such elements. See, e.g., U.S. Patent Application Publication 2019/0275331. Assessments of ECAP features can also be used to determine cardiovascular effects, such as a patient's heart rate. See, e.g., U.S. Patent Application Publication 2019/0290900. To the extent one wishes to assess features of an ECAP that are obscured by a stimulation artifact, U.S. Patent Application Publication 2019/0366094 discloses techniques that can used to extract ECAP features from the ESG signal. As discussed in some of these references, detected ECAPs can also be dependent on a patient's posture or activity, and therefor assessment of ECAP features can be used to infer a patient's posture, which may then in turn be used to adjust the stimulation that the IPG 100 provides.

It can also be useful to detect features of stimulation artifacts 134 in their own right. For example, U.S. Patent Application Publication 2022/0323764 describes that features of stimulation artifacts can be useful to determining patent posture or activity, which again may then in turn be used to adjust the stimulation that the IPG 100 provides.

FIG. 5 shows further details of the circuitry in an IPG 100 that can provide stimulation and sensing an ElectroSpinoGram (ESG) signal. The IPG 100 includes control circuitry 102, which may comprise a microcontroller, such as Part Number MSP430, manufactured by Texas Instruments, Inc., which is described in data sheets at www.ti.com, which are incorporated herein by reference. Other types of controller circuitry may be used in lieu of a microcontroller as well, such as microprocessors, FPGAs, DSPs, or combinations of these, etc. Control circuitry 102 may also be formed in whole or in part in one or more Application Specific Integrated Circuits (ASICs), such as those described and incorporated earlier.

Figures 1, 2A, 2B:
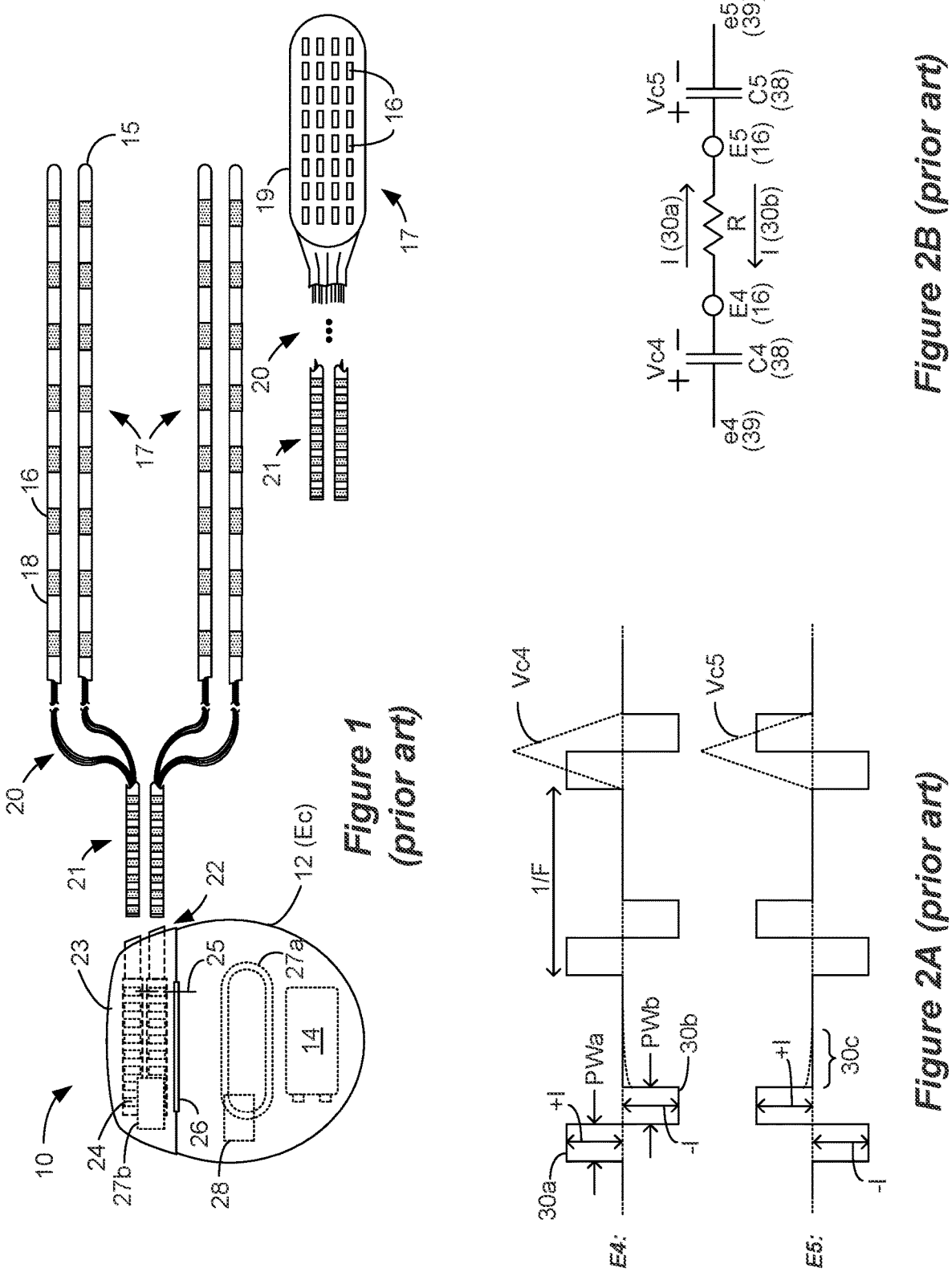
FIG. 1 shows an Implantable Pulse Generator (IPG), in accordance with the prior art.
FIGS. 2A and 2B show an example of stimulation pulses producible by the IPG, in accordance with the prior art.
Figure 3:
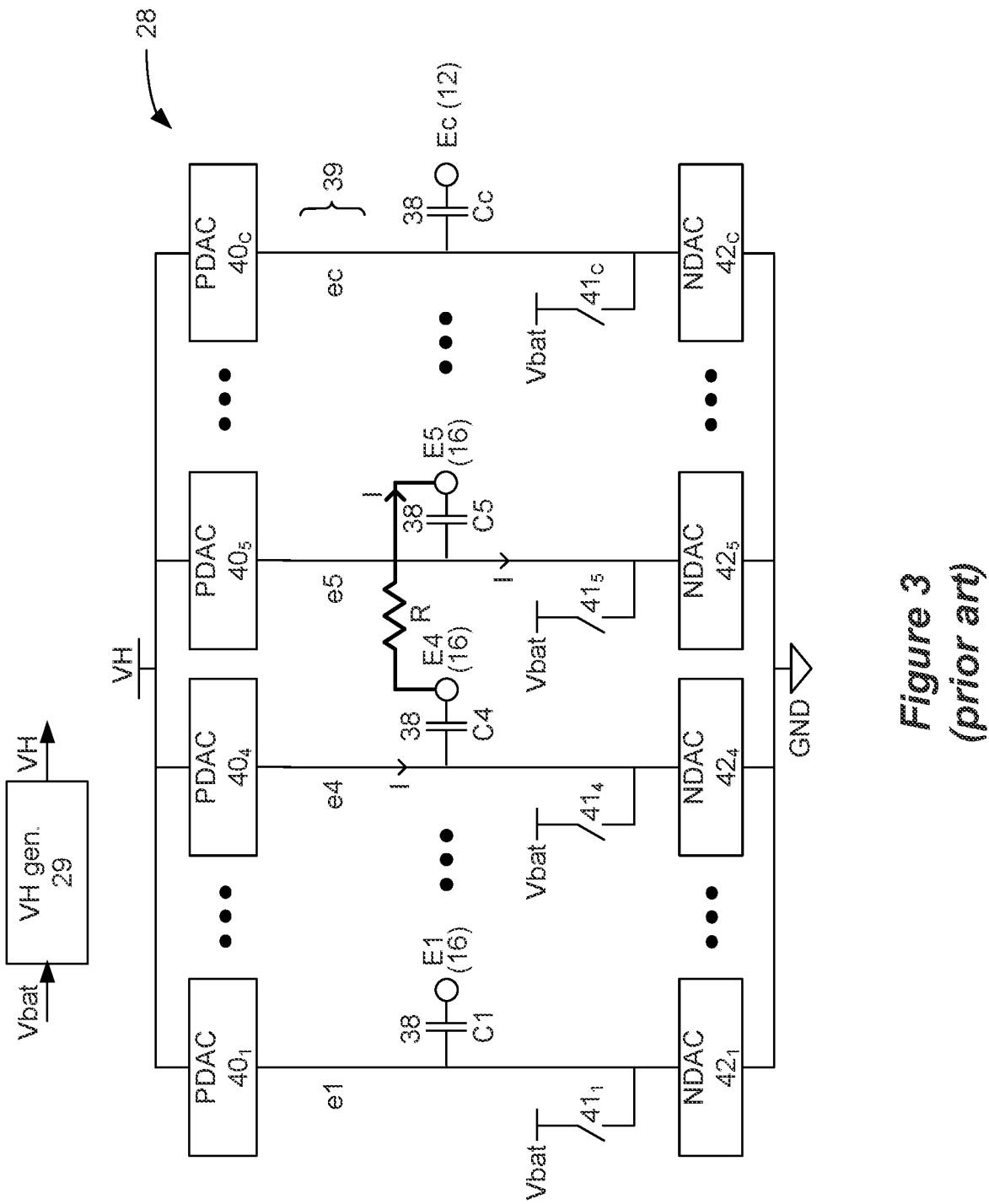
FIG. 3 shows stimulation circuitry useable in the IPG, in accordance with the prior art.
Figure 4:
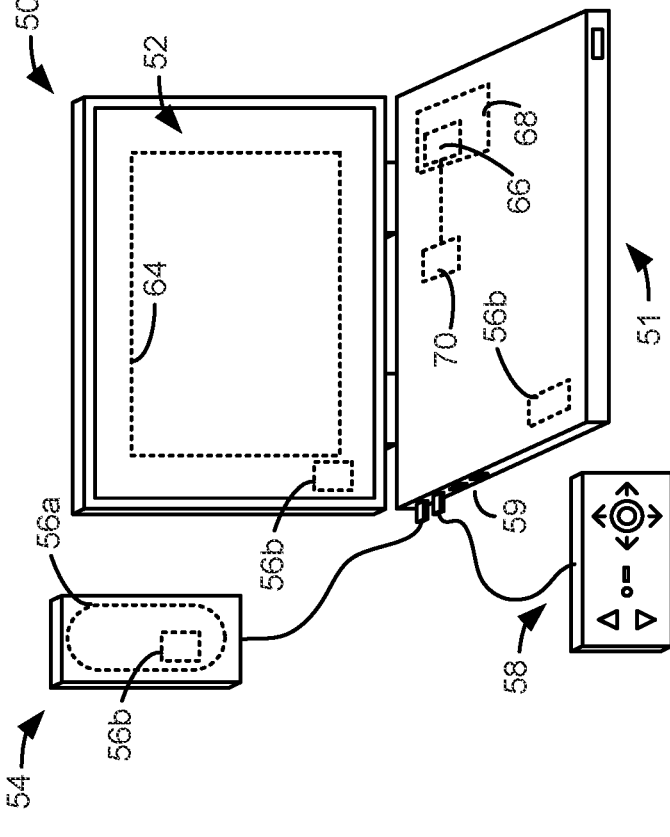
FIG. 4 shows external devices able to communicate with the IPG, in accordance with the prior art.
Figure 4:
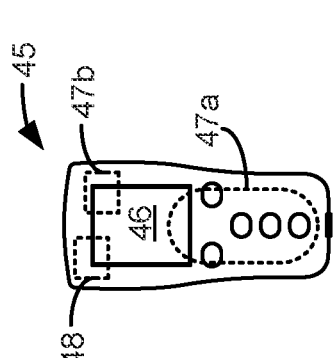

The IPG 100 also includes stimulation circuitry 28 to produce stimulation at the electrodes 16, which may comprise the stimulation circuitry 28 shown earlier (FIG. 3). A bus 118 provides digital control signals from the control circuitry 102 (and possibly from an feature extraction algorithm 140, described below) to one or more PDACs $40_i$ or NDACs $42_i$ to produce currents or voltages of prescribed amplitudes (I) for the stimulation pulses, and with the correct timing (PW, F) at selected electrodes. As noted earlier, the DACs can be powered between a compliance voltage VH and ground. As also noted earlier, but not shown in FIG. 4, switch matrices could intervene between the PDACs and the electrode nodes 39, and between the NDACs and the electrode nodes 39, to route their outputs to one or more of the electrodes, including the conductive case electrode 12 (Ec). Control signals for switch matrices, if present, may also be carried by bus 118. Notice that the current paths to the electrodes 16 include the DC-blocking capacitors 38 described earlier, which provide safety by preventing the inadvertent supply of DC current to an electrode and to a patient's tissue. Passive recovery switches $41_i$ (FIG. 3) could also be present, but are not shown in FIG. 5 for simplicity.

IPG 100 also includes sensing circuitry 115, and one or more of the electrodes 16 can be used to sense signals the ESG signal. In this regard, each electrode node 39 is further coupleable to a sense amp circuit 110. Under control by bus 114, a multiplexer 108 can select one or more electrodes to operate as sensing electrodes (S+, S−) by coupling the electrode(s) to the sense amps circuit 110 at a given time, as explained further below. Although only one multiplexer 108 and sense amp circuit 110 are shown in FIG. 5, there could be more than one. For example, there can be four multiplexer 108/sense amp circuit 110 pairs each operable within one of four timing channels supported by the IPG 100 to provide stimulation. The sensed signals output by the sense amp circuitry are preferably converted to digital signals by one or more Analog-to-Digital converters (ADC(s)) 112, which may sample the output of the sense amp circuit 110 at 50 kHz for example. The ADC(s) 112 may also reside within the control circuitry 102, particularly if the control circuitry 102 has A/D inputs. Multiplexer 108 can also provide a fixed reference voltage, Vamp, to the sense amp circuit 110, as is useful in a single-ended sensing mode (i.e., to set S− to Vamp).

So as not to bypass the safety provided by the DC-blocking capacitors 38, the inputs to the sense amp circuitry 110 are preferably taken from the electrode nodes 39. However, the DC-blocking capacitors 38 will pass AC signal components (while blocking DC components), and thus AC components within the ESG signals being sensed (such as the ECAP and stimulation artifact) will still readily be sensed by the sense amp circuitry 110. In other examples, signals may be sensed directly at the electrodes 16 without passage through intervening capacitors 38.

As noted above, it is preferred to sense an ESG signal differentially, and in this regard, the sense amp circuitry 110 comprises a differential amplifier receiving the sensed signal S+(e.g., E8) at its non-inverting input and the sensing reference S– (e.g., E9) at its inverting input. As one skilled in the art understands, the differential amplifier will subtract S– from S+ at its output, and so will cancel out any common mode voltage from both inputs. This can be useful for example when sensing ECAPs, as it may be useful to subtract the relatively large scale stimulation artifact 134 from the measurement (as much as possible) in this instance. That being said, note that differential sensing will not completely remove the stimulation artifact, because the voltages at the sensing electrodes S+ and S– will not be exactly the same. For one, each will be located at slightly different distances from the stimulation and hence will be at different locations in the electric field 130. Thus, the stimulation artifact 134 can still be sensed even when differential sensing is used. Examples of sense amp circuitry 110, and manner in which such circuitry can be used, can be found in U.S. Patent Application Publications 2019/0299006, 2020/0305744, 2020/0305745 and 2022/0233866.

The digitized ESG signal from the ADC(s) 112—inclusive of any detected ECAPs and stimulation artifacts—is received at a feature extraction algorithm 140 programmed into the IPG's control circuitry 102. The feature extraction algorithm 140 analyzes the digitized sensed signals to determine one or more ECAP features, and one or more stimulation artifact features, as described for example in U.S. Patent Application Publication 2022/0323764. Such features may generally indicate the size and shape of the relevant signals, but may also be indicative of other factors (like ECAP conduction speed). One skilled in the art will understand that the feature extraction algorithm 140 can comprise instructions that can be stored on non-transitory machine-readable media, such as magnetic, optical, or solid-state memories within the IPG 100 (e.g., stored in association with control circuitry 102).

For example, the feature extraction algorithm 140 can determine one or more neural response features (e.g., ECAP features), which may include but are not limited to:

a height of any peak (e.g., N1);

a peak-to-peak height between any two peaks (such as from N1 to P2);

a ratio of peak heights (e.g., N1/P2);

a peak width of any peak (e.g., the full-width half-maximum of N1);

an area or energy under any peak;

a total area or energy comprising the area or energy under positive peaks with the area or energy under negative peaks subtracted or added;

a length of any portion of the curve of the ECAP (e.g., the length of the curve from P1 to N2);

any time defining the duration of at least a portion of the ECAP (e.g., the time from P1 to N2);

a time delay from stimulation to issuance of the ECAP, which is indicative of the neural conduction speed of the ECAP, which can be different in different types of neural tissues;

a conduction speed (i.e., conduction velocity) of the ECAP, which can be determined by sensing the ECAP as it moves past different sensing electrodes;

a rate of variation of any of the previous features, i.e., how such features change over time;

a power (or energy) determined in a specified frequency band (e.g., delta, alpha, beta, gamma, etc.) determined in a specified time window (for example, a time window that overlaps the neural response, the stimulation artifact, etc.);

any mathematical combination or function of these variables;

Such ECAP features may be approximated by the feature extraction algorithm 140. For example, the area under the curve may comprise a sum of the absolute value of the sensed digital samples over a specified time interval. Similarly, curve length may comprise the sum of the absolute value of the difference of consecutive sensed digital samples over a specified time interval. ECAP features may also be determined within particular time intervals, which intervals may be referenced to the start of simulation, or referenced from within the ECAP signal itself (e.g., referenced to peak N1 for example).

In this disclosure, ECAP features, as described above, are also referred to as neural features or neural response features. This is because such ECAP features contain information relating to how various neural elements are excited/recruited during stimulation, and in addition, how these neural elements spontaneously fired producing spontaneous neural responses as well.

The feature extraction algorithm 140 can also determine one or more stimulation artifact features, which may be similar to the ECAP features just described, but which may also be different to account for the stimulation artifact 134's different shape. Determined stimulation artifact features may include but are not limited to:

a height of any peak;

a peak-to-peak height between any two peaks;

a ratio of peak heights;

an area or energy under any peak;

a total area or energy comprising the area or energy under positive peaks with the area or energy under negative peaks subtracted or added;

a length of any portion of the curve of the stimulation artifact;

any time defining the duration of at least a portion of the stimulation artifact;

a rate of variation of any of the previous features, i.e., how such features change over time;

a power (or energy) determined in a specified frequency band (e.g., delta, alpha, beta, gamma, etc.) determined in a specified time window (for example, a time window that overlaps the neural response, the stimulation artifact, etc.);

any mathematical combination or function of these variables.

Again, such stimulation artifact features may be approximated by the feature extraction algorithm 140, and may be determined with respect to particular time intervals, which intervals may be referenced to the start or end of simulation, or referenced from within the stimulation artifact signal itself (e.g., referenced to a particular peak).

Once the feature extraction algorithm 140 determines one or more of these features, it may then be used to any useful effect in the IPG 100, and specifically may be used to adjust the stimulation that the IPG 100 provides, for example by providing new data to the stimulation circuitry 28 via bus

118. This is explained further in some of the U.S. patent documents cited above. For example, if the distance between the stimulation electrode(s) and the patient's spinal cord changes (for example, because of postural changes, coughing, movement, etc.), the stimulation may be adjusted based on the extracted features to maintain optimum therapeutic stimulation.

The SCS/neural sensing patents and applications mentioned above primarily concern ECAPs and/or stimulation artifacts. The inventors have discovered other neural responses that can be sensed, recorded, and put to useful effect during SCS. Without being bound by theory, the inventors hypothesize that the new neural responses originate from synapses and/or are evoked by synapses that connect dorsal column axons with neurons of the dorsal horn. The hypothesis of a synaptic origin of the newly observed signal is supported by the observation that CNQX (AMPA receptor antagonist that inhibits synaptic activity) causes the new neural response to disappear. Accordingly, the new neural responses are referred to in this disclosure as evoked synaptic potentials (ESPs). Since ESPs are neuronal in origin, they may be used as biomarkers for pain, therapeutic window, side effects, and/or paresthesia, as well as for directing the proper placement and control of stimulation.

ESPs differ from stimulation artifacts and ECAPs in several respects. One difference is that the ability to sense ESPs is highly dependent on the location of the sensing electrode(s). Specifically, the ESP is most readily sensed at a location near the synapse from which it originates. The location-sensitivity of ESP sensing contrasts with sensing ECAPs, and/or stimulation artifacts, both of which travel rostrally and caudally from their point of origin, as described above, and therefore may be sensed at various locations along the electrode lead. In other words, the ESP may be sensed at multiple locations along the spinal cord as well (if dorsal column fibers have multiple synaptic entry points into the horn), but not in the spatially continuous way that ECAPs and artifact can be sensed. Thus, ESP sensing locations remain much more constrained than those over which the ECAP may be detectable. Also, an ECAP will exhibit evidence of propagation (i.e., progressive latency changes in N1 and P2) but a relatively consistent morphology. The ESP may also change morphology or even invert, depending on the location of the sensing electrode vs. the neural substrate.

Figure 6:
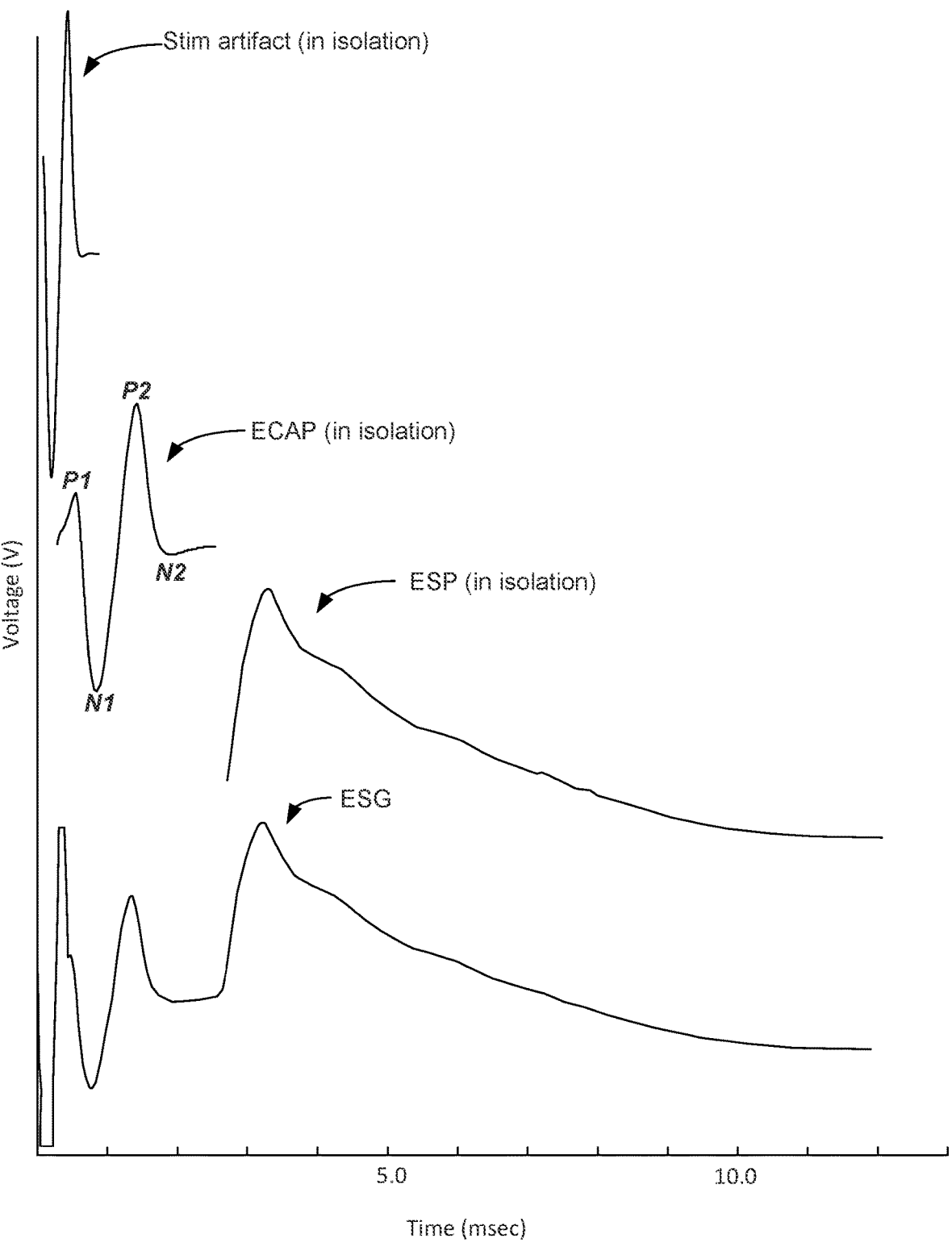
FIG. 6 shows a stimulation artifact, ECAP, and evoked synaptic potential (ESP) each in isolation and combined in an ESG.

ESPs also tend to arise with a longer delay following the stimulation than ECAPs and stimulation artifacts. FIG. 6 illustrates a recorded stimulation artifact, ECAP, and ESP, each in isolation, as well as an ESG that contains each of those three recorded signals. Notice that the ESP occurs later than both the artifact and the ECAP. Accordingly, the contribution of the ESP to the ESG may be distinguished based on the time window during which the signal is recorded, as explained in more detail below.

Another distinguishing feature of ESPs is that they are generally most prominently observed with consistent, relatively unchanging amplitudes when the evoking stimulation frequency is ultra-low, for example, about 10 Hz or less. At higher frequencies, the amplitude of the ESP is significantly reduced after only a small number of periods but may still appear sporadically. In some embodiments, the ESP amplitude evoked with stimulation at 50 Hz starts decreasing after about the fourth pulse and then remain at smaller settled amplitude. With 10 Hz stimulation, the amplitude decreases more slowly, if at all. This is contrasted with ECAPs, which retain their magnitude and morphology even when SCS is applied at relatively higher frequencies (e.g., 50 Hz). Also, ESPs are also correspondingly wider than the ECAPs. ECAP width (defined by N1 to P2 width) may only be 1-5 ms, whereas ESP width, defined roughly as the width of the large positive phase may be or exceed 5-10 ms.

Aspects of this disclosure relate to methods and systems for sensing, recording, characterizing, and using ESPs. For example, aspects of the disclosure involve using one or more features of the ESP as a feedback control variable for adjusting stimulation parameters, as an indication of pain, and/or determining proper placement of stimulation. For example, stimulation parameters and/or stimulation location may be adjusted to maximize a value for one or more features of the ESP. Alternatively, the parameters and/or stimulation location may be adjusted to minimize one or more features of the ESP, for example, if the ESP feature is indicative of a side effect. According to some embodiments, the ESP features may be used in conjunction with features other sensed signals, such as ECAP and/or stimulation artifact signals for feedback control.

Figure 7:
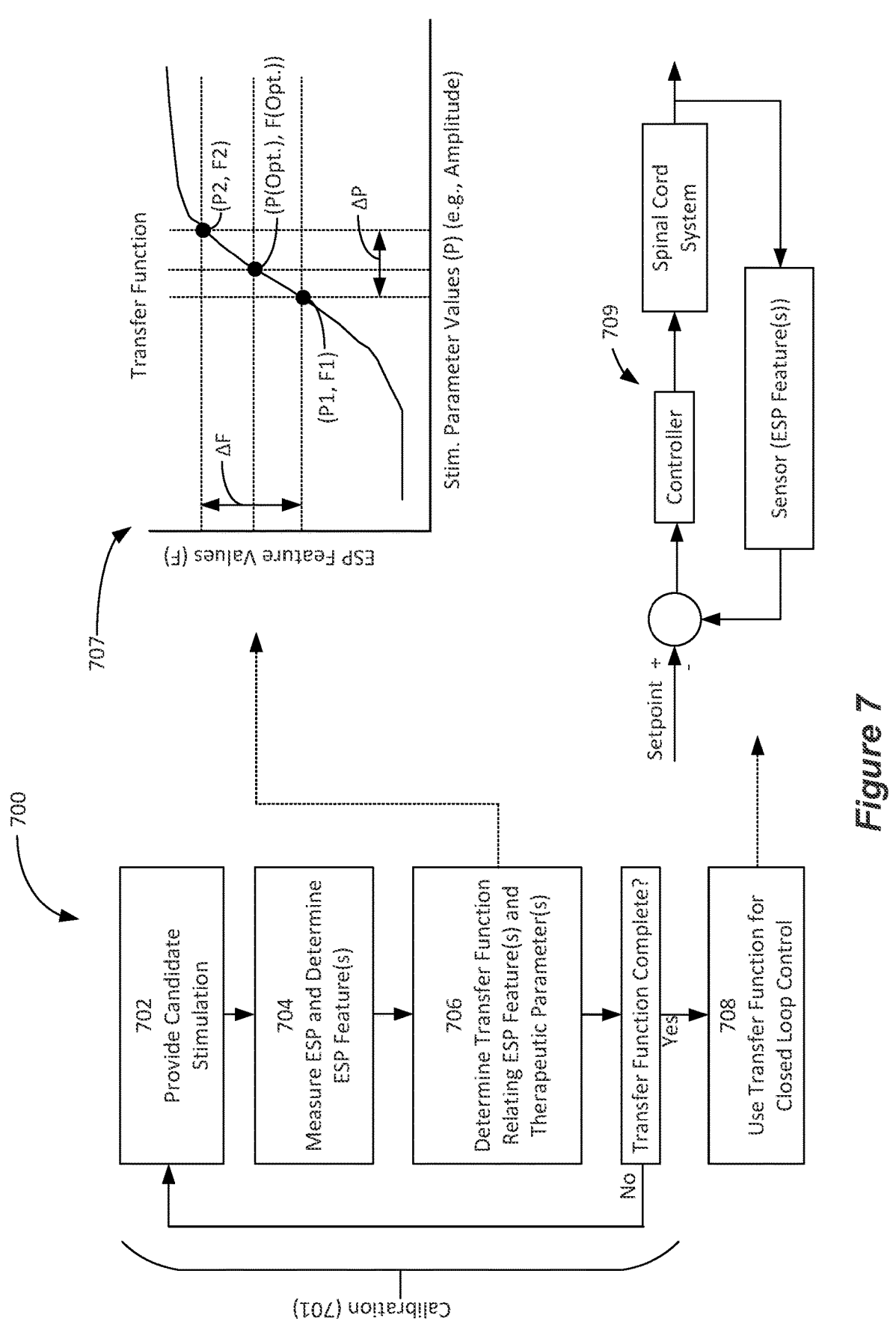
FIG. 7 shows an algorithm for characterizing features of ESPs and using the features for closed loop feedback control of SCS.

FIG. 7 illustrates an algorithm 700 for using ESPs to guide SCS. The algorithm includes calibration aspects 701 and the implementation of closed loop feedback (i.e., step 708). The calibration aspects may be performed in part or in whole using an external device to control the IPG (or ETS), such as the clinician programmer 50 and/or the external controller 45. The implementation of closed loop feedback control may be performed in the IPG, for example, using control circuitry of the IPG.

At step 702, stimulation may be provided to the patient's spinal cord using candidate stimulation parameter values. Example stimulation parameters are described above, and may include, for example, frequency, pulse width, amplitude, inter-phase interval, and the like. The candidate stimulation parameters may also include the location of the stimulation, which may be determined based on the fractionalization of current provided to the selected active electrode contacts. For the purposes of this discussion, assume that the stimulation parameter that the algorithm 700 is seeking to optimize is stimulation amplitude. In that case, step 702 would involve providing stimulation with a first candidate amplitude.

At step 704 an ESP is measured. It should be noted, a precursor step to measuring an ESP may comprise determining an optimum location (i.e., an optimum one or more electrode contacts) at which to measure the ESP. As explained above. the ESP is location dependent, so it may be desirable to poll the various electrode contacts to find an electrode contact or contacts that best sense the ESP.

As explained above, ESPs exhibit consistent and sustained magnitude when evoked at frequencies <10 Hz but could also be observed in response to stimulation having frequencies of Hz or lower. ESPs evoked at higher frequencies may exhibit amplitude decrease over subsequent stimulation periods. If the candidate stimulation waveform has such a frequency, then ESPs evoked by the candidate stimulation waveform may be measured. If the candidate stimulation waveform has a higher frequency, then different stimulation waveforms may need to be applied for the purposes of evoking the ESP or the ESP that is detected according to the criteria above may attenuate over subsequent stimulation periods. In this disclosure, the term "therapeutic stimulation" means stimulation applied for a therapeutic purpose, such as treating the patient's pain. The term "evoking stimulation" applies to stimulation applied for the purpose of evoking ESPs. The evoking stimulation may have a frequency that is particularly configured to evoke ESPs, for example, below 10 Hz. The evoking stimulation may comprise a single pulse, according to some embodiments.

Figure 8:
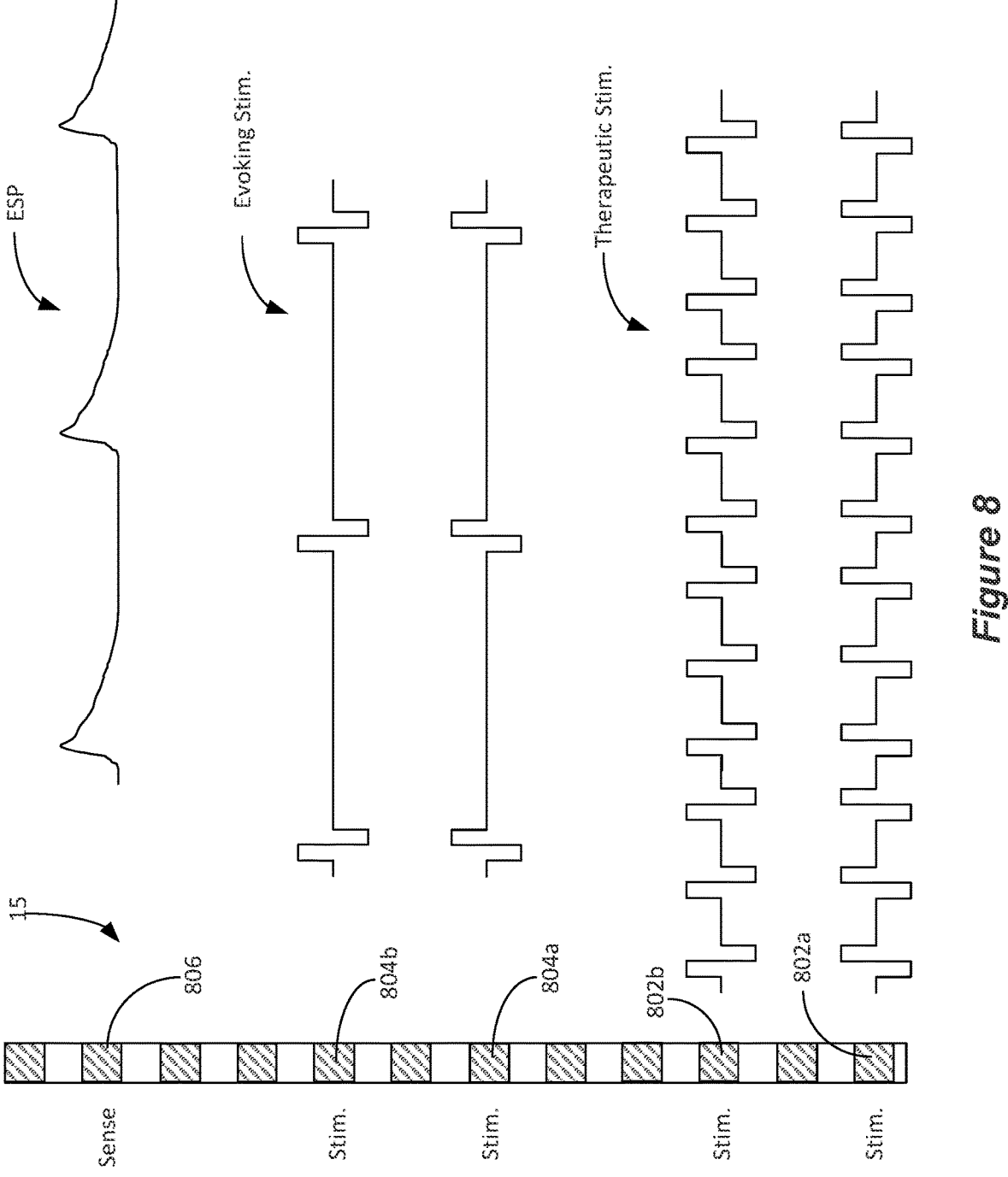
FIG. 8 shows stimulation for evoking and recording ESPs.

FIG. 8 illustrates an embodiment wherein therapeutic stimulation is applied at a first one or more electrode contacts (electrode contacts 802a and 802b, in the illustration) of an electrode lead 15. In the context of step 704 of the algorithm 700 (FIG. 7), the therapeutic stimulation applied at electrode contacts 802a and 802b may be candidate stimulation waveform having the candidate amplitude. Evoking stimulation may be applied simultaneously at a second one or more electrode contacts (804a and 804b, in the illustration). Note that the evoking stimulation can have a lower frequency than the therapeutic stimulation. The evoking stimulation may have an ultra-low frequency, for example, less than 10 Hz. One or more electrode contacts (electrode contact 806, in the illustration) may be used to sense the ESP. Note that the stimulation artifact and ECAP signals are omitted in FIG. 8 ESP signal, for clarity.

Figure 9:
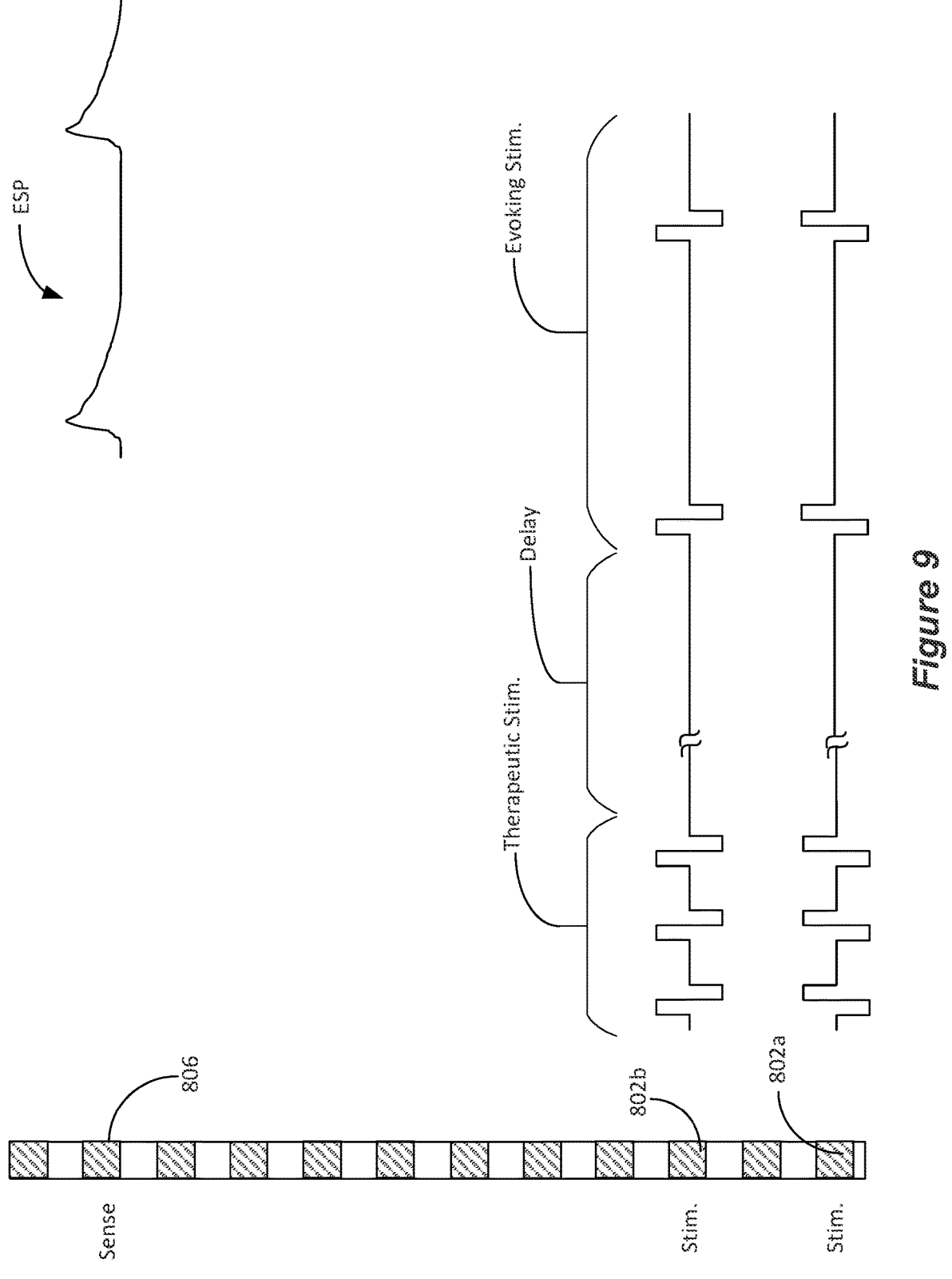
FIG. 9 shows stimulation for evoking and recording ESPs.

FIG. 9 illustrates another embodiment of applying both therapeutic and evoking stimulation. In FIG. 9, therapeutic stimulation is provided at a first one or more electrodes (electrode contacts 802a and 802b, in the illustration) for a first duration. A delay period is imposed for a second duration. Following the delay, evoking stimulation is issued at one or more electrodes, which may (or may not) be the same as the first one or more electrodes. The evoking stimulation is issued for a third duration, during which the ESP may be recorded at one or more recording electrodes contacts (electrode contact 806, in the illustration). The therapeutic stimulation may be resumed following the evoking stimulation, it may be delayed for a further interval.

Referring again to FIG. 7, either of the embodiments illustrated in FIG. 8 or 9 may be used to measure the ESP in response to the candidate stimulation parameters, according to step 704. Also, recall that the ESP typically arises later in time following the evoking stimulation, compared to other detectable responses, such as the stimulation artifacts and/or ECAPs, as shown in FIG. 6. Accordingly, recording the ESP (step 704) may include imposing a delay duration between issuing the evoking stimulation and the beginning of recording at the sensing electrode to avoid (as much as possible/practical) recording the stimulation artifact and the ECAP and only recording the ESP. According to some embodiments, the delay duration may be about 3 milliseconds, 2.5 milliseconds, or 2 milliseconds, etc., following the evoking stimulation, for example. According to some embodiments, the timing of the recording may be keyed to a feature of a sensed stimulation artifact or a sensed ECAP signal. For example, the algorithm may sense a feature of the ECAP, such as the N1 peak of the ECAP, and then wait an additional 1 or 1.5 milliseconds before recording the ESP. Alternatively, the algorithm may sense a feature of the stimulation artifact, such as a rising phase of the stimulation artifact, a settling phase of the artifact, etc., and time the sensing of the ESP based on the artifact feature. Also, as mentioned above, ESPs are also correspondingly wider than the ECAPs. As a consequence, some embodiments involve continuing to sense for 5-10 milliseconds or longer after the beginning of sensing, so as to capture most or all of the ESP signal. According to some embodiments, a sensed putative ESP signal may be rejected if no ECAP signal is present.

Step 704 also comprises determining one or more values for features of the ESP. The determined ESP features may be analogous to any of the features described above that may be determined for stimulation artifacts and/or ECAPs. Examples of ESP features that may be determined may be peak height, area under the curve, curve length, curve shape (such as decay rate), or any of the above-described features.

At step 706, the determined ESP feature(s) are used to develop a relationship, or "transfer function" that relates the one or more ESP features to stimulation parameters that coincide with a therapeutic goal. FIG. 7 illustrates an example of a transfer function 707, wherein ESP feature values (F) are plotted as a function of stimulation parameter values (P). In the illustrated embodiment, stimulation parameters corresponding to an optimum therapeutic outcome may be determined. Examples of therapeutic outcome may relate to pain relief, stimulation location, pain-paresthesia overlap, neural recruitment, etc. A value of a parameter (such as stimulation amplitude, pulse width, rate, total charge delivered per unit time, and/or a parameter envelope function modulation factor) that corresponds to an optimum therapeutic outcome (such as pain relief) may be denoted as P(Opt.) in Figure. For example, the stimulation value P(Opt.) may denote a stimulation amplitude that results in optimum pain relief for the patient. The range of parameter values ($\Delta$P) between P1 and P2 may correspond to a range of stimulation amplitudes that provide acceptable pain relief. For example, the range ($\Delta$P) may correspond to a therapeutic window. The transfer function relates the stimulation parameter values to corresponding values of the one or more ESP features. In other words, an ESP feature value F(Opt.) can be identified that corresponds to the optimum stimulation amplitude (and, accordingly, the optimum pain relief). A range of ESP feature values ($\Delta$F) may be identified that corresponds to the range of stimulation parameter values $\Delta$P. Steps 702-706 may be repeated until a transfer function is determined to adequate precision.

At step 708, the values of the ESP features and the transfer function may be used for closed loop feedback control of stimulation. As mentioned above, the control circuitry with in the IPG may be programmed with one or more sets of instructions configured to cause the IPG to adjust stimulation parameters based on features of the ESP. According to some embodiments, the IPG may be configured to provide therapeutic stimulation and to periodically issue evoking stimulation. The therapeutic stimulation may be sub-perception or paresthesia or a combination of both sub-perception and paresthesia. The evoking stimulation and the therapeutic stimulation may occur simultaneously, as illustrated in FIG. 8, or at different times, as illustrated in FIG. 9. If simultaneously delivered, the device may be configured to stop therapeutic stimulation afterwards for long enough such that the ESP can be sensed, for example if the therapeutic waveform was a high energy waveform. If therapeutic stimulation is being delivered at a rate that is incompatible with the ESP, the device may also be configured to pause therapeutic stimulation for 1-2 seconds before delivering the evoking stimulation.

The IPG may comprise a closed loop feedback control algorithm that is configured to use the one or more ESP feature values as control variables. Closed-loop feedback control is well known in the art and is not discussed here in detail, but the control scheme may involve controllers such PID controllers, Kalman filters, or the like. FIG. 7 illustrates a simplified control diagram 709, whereby a controller (e.g., IPG control circuitry) controls stimulation based on the ESP feature(s) sensed from the patient's spinal cord, as described above. The feedback control algorithm may adjust stimulation parameters to seek to maintain the sensed ESP features with respect to F(Opt.) or within the range $\Delta$F, for example.

Although particular embodiments of the present invention have been shown and described, the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method of sensing evoked synaptic potentials (ESP) evoked in a patient's spinal cord in response to stimulation applied to the patient's spinal cord using one or more electrode leads implantable in the patient's spinal column, each electrode lead comprising a plurality of spinal electrode contacts, the method comprising:

using a first one or more of the spinal electrode contacts to provide evoking stimulation to the patient's spinal cord, wherein the evoking stimulation has a frequency of 50 Hz or less, using a second one or more of the spinal electrode contacts to sense and record the ESP, determining one or more features of the ESP, and using the one or more features for closed loop feedback adjustment of therapeutic stimulation.

2. The method of claim 1, wherein the evoking stimulation has a frequency of 10 Hz or less.

3. The method of claim 1, wherein the evoking stimulation is configured to provide pain relief for the patient.

4. The method of claim 1, wherein the evoking stimulation is configured to be below the patient's perception threshold.

5. The method of claim 1, further comprising using a third one or more of the electrode contacts to provide therapeutic stimulation to the patient's spinal cord, wherein the therapeutic stimulation has a frequency of greater than 30 Hz.

6. The method of claim 5, wherein the third one or more of the electrode contacts are different than the first one or more electrode contacts.

7. The method of claim 5, wherein the third one or more of the electrode contacts are the same as the first one or more electrode contacts.

8. The method of claim 5, wherein providing the therapeutic stimulation and the evoking stimulation comprises:

using the first one or more electrode contacts to provide the therapeutic stimulation for a first duration, following the first duration, applying no stimulation for a second duration at the first one or more electrode contacts, and following the second duration, using the third one or more electrode contacts to provide the evoking stimulation.

9. The method of claim 5, wherein the therapeutic stimulation is configured to provide pain relief to the patient.

10. The method of claim 5, wherein the therapeutic stimulation is configured to provide paresthesia that overlaps pain in the patient's body.

11. The method of claim 5 wherein the therapeutic stimulation is below a perception threshold of the patient.

12. The method of claim 1, wherein the closed loop feedback adjustment is configured to maintain the therapeutic stimulation within a therapeutic window.

13. The method of claim 12, wherein the closed loop feedback adjustment is configured to maintain paresthesia-pain overlap.

14. A system for providing electrical stimulation to a patient's spinal cord to treat pain in the patient using one or more electrode leads implantable in the patient's spinal column, each electrode lead comprising a plurality of spinal electrode contacts, the system comprising:

a neurostimulator that is connectable to the one or more electrode leads, and control circuitry configured to:

use a first one or more of the spinal electrode contacts to provide evoking stimulation to the patient's spinal cord, wherein the evoking stimulation has a frequency of 50 Hz or less, and use a second one or more of the spinal electrode contacts to record evoked synaptic potentials (ESP) evoked in the patient's spinal cord in response to the stimulation, determine one or more features of the ESP, and use the one or more features for closed loop feedback adjustment of therapeutic stimulation.

15. The system of claim 14, wherein the evoking stimulation has a frequency of 10 Hz or less.

16. The system of claim 14, wherein the control circuitry is configured to use a third one or more of the electrode contacts to provide therapeutic stimulation to the patient's spinal cord, wherein the therapeutic stimulation has a frequency of greater than 30 Hz.

17. The system of claim 16, wherein the third one or more of the electrode contacts is different than the first one or more electrode contacts.

18. The system of claim 16, wherein the third one or more of the electrode contacts is the same as the first one or more of the electrode contacts.

*    *    *    *    *